US010668141B2

(12) United States Patent
Ito et al.

(10) Patent No.: US 10,668,141 B2
(45) Date of Patent: Jun. 2, 2020

(54) **VACCINE CONTAINING INACTIVATED CELLS OF *STAPHYLOCOCCUS AUREUS* MIXED WITH LEUCOCIDIN**

(71) Applicant: Kyoto Biken Laboratories, Inc., Kyoto (JP)

(72) Inventors: Toshihiro Ito, Uji (JP); Taichi Noro, Uji (JP)

(73) Assignee: Kyoto Biken Laboratories, Inc., Kyoto (JP)

( * ) Notice: Subject to any disclaimer, the term of this patent is extended or adjusted under 35 U.S.C. 154(b) by 0 days.

(21) Appl. No.: 15/751,123

(22) PCT Filed: Jul. 29, 2016

(86) PCT No.: PCT/JP2016/072313
§ 371 (c)(1),
(2) Date: Feb. 7, 2018

(87) PCT Pub. No.: WO2017/026301
PCT Pub. Date: Feb. 16, 2017

(65) Prior Publication Data
US 2018/0228884 A1  Aug. 16, 2018

(30) Foreign Application Priority Data
Aug. 10, 2015 (JP) ................................ 2015-158323

(51) Int. Cl.
| | |
|---|---|
| *A01N 63/00* | (2020.01) |
| *A61K 39/09* | (2006.01) |
| *A61K 39/085* | (2006.01) |
| *A61K 39/38* | (2006.01) |
| *A61K 45/00* | (2006.01) |
| *A61K 47/00* | (2006.01) |
| *C07K 14/31* | (2006.01) |
| *A61P 31/04* | (2006.01) |
| *A61K 39/00* | (2006.01) |

(52) U.S. Cl.
CPC ............ *A61K 39/085* (2013.01); *A61P 31/04* (2018.01); *C07K 14/31* (2013.01); *A61K 2039/521* (2013.01); *A61K 2039/552* (2013.01)

(58) Field of Classification Search
CPC ........ A61K 35/74; A61K 8/99; A61K 39/085; C07K 14/315
See application file for complete search history.

(56) References Cited

U.S. PATENT DOCUMENTS

2008/0131457 A1* 6/2008 Taylor .................. A61K 39/085
424/203.1

FOREIGN PATENT DOCUMENTS

| JP | H3-056426 A | 3/1991 |
| JP | 2009-286730 A | 12/2009 |
| JP | 2012-514602 A | 6/2012 |
| JP | 2012514602 * | 6/2012 |
| WO | WO 2013/082558 A1 * | 6/2013 |

OTHER PUBLICATIONS

Rainard, Veterinary Research, 2007; 38(5): 685-696 (Year: 2007).*
Padmaja et al., Veterinary Microbiology, 2014; 170: 358-367 (Year: 2014).*
Peterson-Wolfe et al., Virginia Cooperative Extension, 2010; publication 404-229; pp. 1-7 (Year: 2010).*
Vrieling et al., JAG, 2015; 6(3): e00335-15 (Year: 2015).*
Bowie et al., Science, 1990, 257:1306-1310 (Year: 1990).*
Zou et al., Biosci. Biotechnol. Biochem., 2000; 64(12): 2631-2643 (Year: 2000).*
International Search Report dated Oct. 25, 2016, issued in corresponding International Patent Application No. PCT/JP2016/072313 and English translation of the same. (4 pages).
Vrieling, M. et al.; Bovine *Staphylococcus aureus* Secretes the Leukocidin LukMF' to Kill Migrating Neutrophils through CCRI; MBio; May 2015; vol. 6; Issue 3; p. 1-9.
Barrio, M. et al.; LukM/LukF'-PV is the most active *Staphylococcus aureus* leukotoxin on bovine neutrophils; Microbes and Infection; May 26, 2006; vol. 8; p. 2068-2074.
Rainard et al.; "Leucotoxic Activities of *Staphylococcus aureus* Strains Isolated from Cows, Ewes and Goats with Mastitis: Importance of LukM/LukF'-PV Leukotoxin"; Clinical and Diagnostic Laboratory Immunology, Mar. 2003; vol. 10, No. 2; p. 272-277.
Younis et al.; "*Staphylococcus aureus* Exosecretions and Bovine Mastitis"; J. Vet. Med. B 50, 2003; p. 1-7.
Rainard; "*Staphylococcus aureus* leucotoxin LukM/F' is secreted and stimulates neutralising antibody response in the curse of intramammary infection"; Vet. Res. 38, 2007; p. 685-696.

* cited by examiner

*Primary Examiner* — Gary B Nickol
*Assistant Examiner* — Lakia J Jackson-Tongue
(74) *Attorney, Agent, or Firm* — Fitch, Even, Tabin & Flannery LLP

(57) ABSTRACT

An immunogenic composition containing leucocidin M/F antigen and capable of imparting a toxin-neutralizing activity to a ruminant animal as a subject animal. The immunogenic composition enables prevention of onset or reduction in symptoms of diseases caused by *Staphylococcus aureus* in ruminant animals. The leucocidin M/F antigen is a protein or peptide having at least a part of the amino acid sequence constituting the leucocidin M protein or a protein or peptide having at least a part of the amino acid sequence constituting the leucocidin F protein. The immunogenic composition may further contain a somatic antigen of *Staphylococcus aureus*.

9 Claims, 4 Drawing Sheets
Specification includes a Sequence Listing.

*The values represent geometric means of attacked breasts.

*Because of seriously exacerbated mastitis in the control cow, no milk was collected from the control cow after 96 hours or later.

SEQUENCE LISTING

<160> NUMBER OF SEQ ID NOS: 4

<210> SEQ ID NO 1
<211> LENGTH: 927
<212> TYPE: DNA
<213> ORGANISM: Artificial Sequence
<220> FEATURE:
<223> OTHER INFORMATION: Description of Artificial Sequence :LukM

<400> SEQUENCE: 1

```
atgtttaaga gaaaattatt agttacaact ttgtcgctag gtctaattgt ccctatagct    60
acaccatttc aaggctctaa ggctactact aatgcagaag atattggcga cgatgcagaa   120
gtgattaaac gtacggaaga tgtaagtagt aggaaatggg gtgtaacaca aaatgtccaa   180
tttgatttcg taaaagataa aaaatataac aaagacgcat taattattaa gatgcaaggt   240
tttatcaatt ctaggacaac tttcaatgat gttaaacaaa atagagcaaa taaagaatg   300 gtttggccat ttcaatataa tatcggtctt acatcaaaag accaaaatac gagcttaatc   360
aattatcttc ctaaaaataa aatagaaaca gttgatgttg gtcaaacttt aggatataac   420
attggaggta aattccagtc agtaccatct ataggcggaa atggatcatt taattattct   480
```

-continued

| aagagtatta aatattccca aaagagttat gtcagcgaag ttgaacaaca aagctcaaaa | 540 |
| actattaagt gggggttaa agcaaattct tttgttatag cagggcatcg atggtctgct | 600 |
| tacgatgaat tattgtttat aagaaatacg acaagaggac ctaatgctag agactatttt | 660 |
| gtagacgata atgaattgcc ccctttaata acaagtggat taatccgtc ttttatcgcg | 720 |
| acagtatctc acgaaaaaga ttcaggcgat acgagcgaat ttgaaattac ttacggtaga | 780 |
| aatatggatg ttacctatgc aacctacctt cctaaacttg gtctttatcc agaaagaaaa | 840 |
| cataatgaat ttgtaaacag aaactttgtg gtcaaatatg aagtgaattg gaaaacgtac | 900 |
| gaaattaaag taaaggggca caactaa | 927 |

<210> SEQ ID NO 2
<211> LENGTH: 969
<212> TYPE: DNA
<213> ORGANISM: Artificial Sequence
<220> FEATURE:
<223> OTHER INFORMATION: Description of Artificial Sequence :LukF

<400> SEQUENCE: 2

| atgaaattta agaatatagt caaatcatca gtcgctacat caattacatt aatcatgcta | 60 |
| tcaaatacag ttgatgcagc tcaacatatc acacctgtca gcgagaaaaa agtggatgac | 120 |
| aaaatcactt tgtacaaaac gactgctaca tcagattctg acaaattaaa aatttctcaa | 180 |
| attctaactt taattttat aaagacaaa agttatgata agacacatt aatactaaaa | 240 |
| gctgccggaa acatttactc aggctatacc caacccactt ctgatagtag tataaattca | 300 |
| caattttatt ggggagctaa gtataatgtt tttgttagct cggagtccaa agattctgta | 360 |
| aatattgttg actacgcgcc taaaaatcaa aatgaagaat tcaagttca acaaacatta | 420 |
| ggttattcat atggcggaga tattaatata ataaatggat taactggtgg attgaatggg | 480 |
| tcaaaatcat tttcagaaac gattaattat aagcaagaaa gctacagaac tacgattgat | 540 |
| aggaaaacaa atcataaatc aatcggctgg ggtgtcgagg cacataaaat catgaataat | 600 |
| ggttggggc catatggcag agatagtagt gattcattat atggaaacga actattttta | 660 |
| ggtggcagac agagtagctc gaatgctaat caaaattct taccaacaca tcaaatgccc | 720 |
| atattagcac gtggtaattt caatccagaa tttataagcg tactttctca caaacaaaag | 780 |
| gatgttaaaa aatctaaaat taagtgact tatcaaagag aaatggatcg gtatgaaaat | 840 |
| ttttggaaca acttgcactg gataggttat aatattaaga atcaaaagag agcaacacac | 900 |
| acatcaattt atgaaattga ttgggaaaaa cacacggtta aattagtagc ttcgcaatct | 960 |
| agcgaataa | 969 |

<210> SEQ ID NO 3
<211> LENGTH: 308
<212> TYPE: PRT
<213> ORGANISM: Artificial Sequence
<220> FEATURE:
<223> OTHER INFORMATION: Description of Artificial Sequence :LukM

<400> SEQUENCE: 3

Met Phe Lys Arg Lys Leu Leu Val Thr Thr Leu Ser Leu Gly Leu Ile
1               5                   10                  15

Val Pro Ile Ala Thr Pro Phe Gln Gly Ser Lys Ala Thr Thr Asn Ala
            20                  25                  30

Glu Asp Ile Gly Asp Asp Ala Glu Val Ile Lys Arg Thr Glu Asp Val
        35                  40                  45

-continued

Ser Ser Arg Lys Trp Gly Val Thr Gln Asn Val Gln Phe Asp Phe Val
    50              55              60

Lys Asp Lys Lys Tyr Asn Lys Asp Ala Leu Ile Ile Lys Met Gln Gly
65              70              75              80

Phe Ile Asn Ser Arg Thr Thr Phe Asn Asp Val Lys Gln Asn Arg Ala
                85              90              95

Asn Lys Arg Met Val Trp Pro Phe Gln Tyr Asn Ile Gly Leu Thr Ser
            100             105             110

Lys Asp Gln Asn Thr Ser Leu Ile Asn Tyr Leu Pro Lys Asn Lys Ile
            115             120             125

Glu Thr Val Asp Val Gly Gln Thr Leu Gly Tyr Asn Ile Gly Gly Lys
    130             135             140

Phe Gln Ser Val Pro Ser Ile Gly Gly Asn Gly Ser Phe Asn Tyr Ser
145             150             155             160

Lys Ser Ile Lys Tyr Ser Gln Lys Ser Tyr Val Ser Glu Val Glu Gln
                165             170             175

Gln Ser Ser Lys Thr Ile Lys Trp Gly Val Lys Ala Asn Ser Phe Val
            180             185             190

Ile Ala Gly His Arg Trp Ser Ala Tyr Asp Glu Leu Leu Phe Ile Arg
        195             200             205

Asn Thr Thr Arg Gly Pro Asn Ala Arg Asp Tyr Phe Val Asp Asp Asn
    210             215             220

Glu Leu Pro Pro Leu Ile Thr Ser Gly Phe Asn Pro Ser Phe Ile Ala
225             230             235             240

Thr Val Ser His Glu Lys Asp Ser Gly Asp Thr Ser Glu Phe Glu Ile
                245             250             255

Thr Tyr Gly Arg Asn Met Asp Val Thr Tyr Ala Thr Tyr Leu Pro Lys
            260             265             270

Leu Gly Leu Tyr Pro Glu Arg Lys His Asn Glu Phe Val Asn Arg Asn
        275             280             285

Phe Val Val Lys Tyr Glu Val Asn Trp Lys Thr Tyr Glu Ile Lys Val
    290             295             300

Lys Gly His Asn
305

<210> SEQ ID NO 4
<211> LENGTH: 322
<212> TYPE: PRT
<213> ORGANISM: Artificial Sequence
<220> FEATURE:
<223> OTHER INFORMATION: Description of Artificial Sequence :LukF

<400> SEQUENCE: 4

Met Lys Phe Lys Asn Ile Val Lys Ser Ser Val Ala Thr Ser Ile Thr
1               5               10              15

Leu Ile Met Leu Ser Asn Thr Val Asp Ala Ala Gln His Ile Thr Pro
            20              25              30

Val Ser Glu Lys Lys Val Asp Asp Lys Ile Thr Leu Tyr Lys Thr Thr
        35              40              45

Ala Thr Ser Asp Ser Asp Lys Leu Lys Ile Ser Gln Ile Leu Thr Phe
    50              55              60

Asn Phe Ile Lys Asp Lys Ser Tyr Asp Lys Asp Thr Leu Ile Leu Lys
65              70              75              80

Ala Ala Gly Asn Ile Tyr Ser Gly Tyr Thr Gln Pro Thr Ser Asp Ser
                85              90              95

-continued

```
Ser Ile Asn Ser Gln Phe Tyr Trp Gly Ala Lys Tyr Asn Val Phe Val
            100                 105                 110

Ser Ser Glu Ser Lys Asp Ser Val Asn Ile Val Asp Tyr Ala Pro Lys
        115                 120                 125

Asn Gln Asn Glu Glu Phe Gln Val Gln Gln Thr Leu Gly Tyr Ser Tyr
        130                 135                 140

Gly Gly Asp Ile Asn Ile Ile Asn Gly Leu Thr Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Ser Asp Ser Leu Tyr Gly Asn Glu Leu Phe Leu Gly Gly Arg Gln
        210                 215                 220

Ser Ser Ser Asn Ala Asn Gln Asn Phe Leu Pro Thr His Gln Met Pro
225                 230                 235                 240

Ile Leu Ala Arg Gly Asn Phe Asn Pro Glu Phe Ile Ser Val Leu Ser
                245                 250                 255

His Lys Gln Lys Asp Val Lys Lys Ser Lys Ile Lys Val Thr Tyr Gln
            260                 265                 270

Arg Glu Met Asp Arg Tyr Glu Asn Phe Trp Asn Asn Leu His Trp Ile
            275                 280                 285

Gly Tyr Asn Ile Lys Asn Gln Lys Arg Ala Thr His Thr Ser Ile Tyr
        290                 295                 300

Glu Ile Asp Trp Glu Lys His Thr Val Lys Leu Val Ala Ser Gln Ser
305                 310                 315                 320

Ser Glu
```

VACCINE CONTAINING INACTIVATED CELLS OF *STAPHYLOCOCCUS AUREUS* MIXED WITH LEUCOCIDIN

CROSS-REFERENCE TO RELATED APPLICATIONS

This application is a U.S. national phase application filed under 35 U.S.C. § 371 of International Application PCT/JP2016/072313, filed on Jul. 29, 2016, designating the United States, which claims priority from Japanese Application Number 2015-158323, filed Aug. 10, 2015, which are hereby incorporated herein by reference in their entirety.

REFERENCE TO A SEQUENCE LISTING

The Sequence Listing associated with this application is filed in electronic format via EFS-Web and is hereby incorporated into the specification in its entirety. The name of the text file containing the Sequence Listing is "142270_SequenceListing." The size of the text file is 8.0 KB, and the text file was created on Feb. 16, 2018.

TECHNICAL FIELD

The present invention relates to a vaccine for protecting a ruminant animal from a disease (mastitis) caused by *Staphylococcus aureus* (*S. aureus*).

BACKGROUND ART

*Staphylococcus aureus* is one of *Staphylococcus* microorganisms which are resident bacteria on human or animal skins or digestive tracts (intestines) (enteric bacteria), and known as one of the bacteria causing purulent diseases or food poisoning in humans or animals. It is also known that, even when an animal infected with food poisoning-causing bacteria is free itself from any symptoms, there is a possibility that a human in contact with this animal is infected with the food poisoning-causing bacteria or that the food poisoning-causing bacteria is deposited on a product made from this animal, resulting in a significant reduction in the value of the animal itself or the value of the product made from this animal. Amongst, *Staphylococcus aureus* is believed to be related strongly with mastitis in cows.

The annual economical loss due to cow mastitis is reported to be 60 billion yens in Japan. *Staphylococcus aureus* is one of major pathogens which cause cow infectious mastitis, and considered to be treated less effectively with antibiotics unlike to environmental mastitis bacteria such as *Escherichia coli* and environmental *Streptococcus*.

There are at least 30 known pathogenic factors as cell components of *Staphylococcus aureus*, and Protein A, fibronectin-binding protein, clumping factor, and lipoteichoic acid are known as molecules localized in cells. In addition, coagulase and staphylokinase are known as enzymes relating to the pathogenicity.

Those known as toxins released out of cells are those in the enterotoxin group related strongly with food poisoning in humans, TSST-1 related to sepsis and leucocidin exerting a cytotoxic activity to leucocytes as immunocompetent cells.

While investigations focusing mainly on cell components have been made so far as approaches to vaccines for *Staphylococcus aureus*-related mastitis, it is still unsuccessful in discovering a main component which has an evident infection-preventing effect. This is because partly of difficulty in obtaining a preventive effect attributable to a single molecule due to the isolate-based variation in the situation of holding pathogenic factors as cell components. To overcome this, an attempt was made to use a vaccine employing all cells as antigens, but it was unsuccessful in imparting an evident infection-preventing effect similarly to the cases described above. This may partly be caused by such a background that the immune imparted to a milk is insufficient or the evaluation itself is not conducted in most of the cases. While use of a supernatant component as a vaccine antigen is also investigated, a study considering the actual condition of the mastitis-derived microorganisms as active ingredients contained in the supernatant has not been made yet, resulting in a difficulty in imparting infection-preventing effect. It is also believed that it is difficult, only with the supernatant component, to obtain an infection-preventing effect which is sufficient also immunologically. The background is considered to be responsible for unsuccessful development so far of vaccines effective to *Staphylococcus aureus*-related cow mastitis.

There are known technologies for preventing infection with *Staphylococcus aureus* including a mastitis vaccine using *Staphylococcus aureus* as an immunogen which is contained in a vaccine vehicle constituted from a liposome containing methylglutarylated poly(glycidol) (Patent Document 1) or a method for treating or preventing *Staphylococcus aureus* (*S. aureus*) infection in avian or mammalian animals by administering a therapeutically effective amount of a pharmaceutical composition including one or more digestive enzymes to the avian or mammalian animals (Patent Document 2). However, vaccines capable of being used for mastitis, including other pathogens, in actual sites of use such as farms do not exist currently in Japan.

CITATION LIST

Patent Literature

Patent Document 1: JP-A No. 2009-286730
Patent Document 2: JP-T No. 2012-514602

Non-Patent Literature

Non-Patent Document 1: Rainard et al., Clin Diagn Lab Immunol. 2003; 10(2):272-277
Non-Patent Document 2: Younis et al., J Vet Med B Infect Dis Vet Public Health. 2003; 50(1):1-7.
Non-Patent Document 3: Rainard et al., Vet Res. 2007 38(5):685-696.

SUMMARY OF THE INVENTION

Technical Problem

An object of the present invention is to provide an immunogenic composition enabling prevention of onset or reduction in symptoms of diseases caused by *Staphylococcus aureus* in ruminant animals.

Another object of the present invention is to provide a method for inducing an immune response to *Staphylococcus aureus* by administering the immunogenic composition to ruminant animals.

Solution to Problem

We made an intensive study for solving the problems and finally discovered, by focusing on leucocidin M/F as a Staphylococcal toxin, that allowing an antibody against this toxin to be produced in vivo in a subject animal is effective in preventing bovine mastitis infection for example in farms.

We also discovered that the prevention of bovine mastitis infection becomes more efficient by using a somatic antigen of *Staphylococcus aureus* in addition to the leucocidin M/F antigen.

The present invention has been established by the inventors based on the findings.

Thus, aspects of the present invention relate to:

[1] An immunogenic composition containing leucocidin M/F antigen and capable of imparting a toxin-neutralizing activity to a ruminant animal as a subject animal.

[2] The immunogenic composition according to the aforementioned [1], wherein the leucocidin M/F antigen includes: a protein or peptide having at least a part of an amino acid sequence constituting a leucocidin M protein; or a protein or peptide having at least a part of an amino acid sequence constituting a leucocidin F protein.

[3] The immunogenic composition according to the aforementioned [1], wherein the leucocidin M/F antigen includes: a protein or peptide having at least a part of an amino acid sequence constituting a leucocidin M protein; and a protein or peptide having at least a part of an amino acid sequence constituting a leucocidin F protein.

[4] The immunogenic composition according to any of the aforementioned [1] to [3], wherein the leucocidin M/F antigen is obtained from a culture supernatant of *Staphylococcus aureus*.

[5] The immunogenic composition according to any of the aforementioned [1] to [3], wherein the leucocidin M/F antigen is synthesized.

[6] The immunogenic composition according to any of the aforementioned [1] to [5], wherein the leucocidin M/F antigen is inactivated.

[7] The immunogenic composition according to any of the aforementioned [1] to [6], further containing a somatic antigen of *Staphylococcus aureus*.

[8] The immunogenic composition according to the aforementioned [7], wherein the somatic antigen of the *Staphylococcus aureus* is an inactivated whole cell of *Staphylococcus aureus* or a part thereof.

[9] The immunogenic composition according to the aforementioned [7] or [8], wherein the *Staphylococcus aureus* is a *Staphylococcus aureus* separated from a milk of the ruminant animal.

[10] The immunogenic composition according to any of the aforementioned [1] to [9], wherein the ruminant animal is a cow, a goat, a sheep, or a deer.

[11] The immunogenic composition according to any of the aforementioned [1] to [10] for use as a vaccine.

[12] The immunogenic composition according to any of the aforementioned [1] to [10] for use in preparing a formulation for treatment or prevention of diseases related to *Staphylococcus aureus* in the ruminant animal.

[13] A method for inducing an immune response to *Staphylococcus aureus*, the method including administrating the immunogenic composition according to any of the aforementioned [1] to [12] in an immunologically effective amount to a ruminant animal as a subject animal.

[14] The method according to the aforementioned [13] wherein the immune response prevents or reduces a disease or a symptom relating to the *Staphylococcus aureus* in the ruminant animal.

Advantageous Effects of Invention

The immunogenic composition according to the present invention is used, thereby allowing a positive preventive means to be provided for preventing a disease derived from the *Staphylococcus aureus* such as mastitis in ruminant animals including a cow, in addition to the symptomatic therapy using existing antibiotic treatment and sanitary practice for preventing infections.

DESCRIPTION OF EMBODIMENTS

Figure 1:
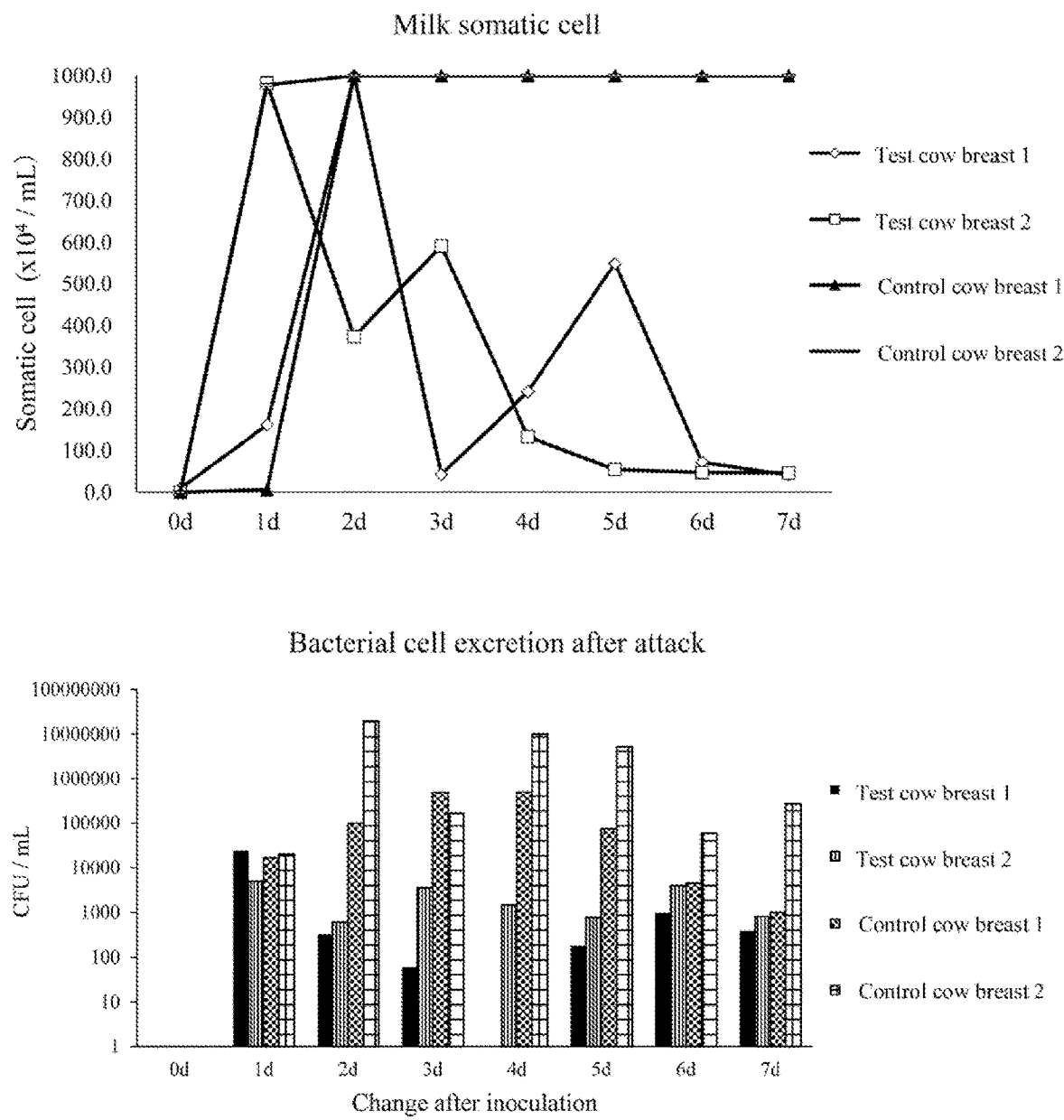
FIG. 1 is a graph showing the results of the onset prevention test conducted in Example 3 using inactivated somatic antigen of *S. aureus* HK-3 strain. In the upper figure, the ordinate indicates somatic cell count per mL of the milk and the abscissa indicates the number of days (d). In the lower figure, the ordinate indicates bacterial cell count per mL of the milk and the abscissa indicates the number of days (d) (the same applies to the upper and lower figures in FIG. 3).

As used herein, "toxin-neutralizing activity" refers to an activity to neutralize the effect of a toxin of leucocidin M/F, which is a bacterial toxin produced by *Staphylococcus aureus*, when administering an immunogenic composition according to the present invention to a ruminant animal.

The fact that the toxin-neutralizing activity can be imparted to a ruminant animal can typically be verified based on the procedure described later in Examples.

As used herein, "immunogenicity" refers to a tendency to induce the production of an antibody against the leucocidin M/F and whole cells of *S. aureus* by stimulating the immune system of a ruminant animal as a subject animal. Meanwhile, "immunogenic composition" refers to a composition inducing an immune response in a ruminant animal when administered to such a ruminant animal.

In the present invention, the ruminant animal as a subject animal may for example be a cow, a goat, a sheep, or a deer. Among these, the cow is preferred because an effective prevention of a disease posing a substantial economic loss to a farmer, for example cow mastitis, can be achieved.

The present invention is an immunogenic composition containing a leucocidin M/F antigen and capable of imparting a toxin-neutralizing activity to a ruminant animal as a subject animal.

The "leucocidin M/F" refers to one of bacterial toxins produced by *Staphylococcus aureus*, and refers to a dimer formed by binding leucocidin M protein (LukM) and leucocidin F protein (LukF). It is known that the leucocidin M protein has an activity to bind to neutrophils while the leucocidin F protein has a cytotoxic activity to neutrophils.

The leucocidin M protein consists of an amino acid sequence (SEQ ID NO: 3) consisting of 308 amino acid residues, which is encoded by a base sequence represented by SEQ ID NO: 1 consisting of 927-bp in the gene sequence possessed by *Staphylococcus aureus*.

On the other hand, the leucocidin F protein consists of an amino acid sequence (SEQ ID NO: 4) consisting of 322 amino acid residues, which is encoded by a base sequence represented by SEQ ID NO consisting of 969-bp: 2 via a 1-bp base downstream of the gene region encoding the leucocidin M protein.

The amino acid sequences and the base sequences of the leucocidin M protein and the leucocidin F protein can be confirmed by any known databases. The known databases may for example be DNA Data Bank of Japan, Medline, and the like.

As used herein, a "leucocidin M/F antigen" refers to an antigen which can allow an antibody capable of binding to a leucocidin M/F to be produced in a ruminant animal as a subject animal.

The leucocidin M/F antigen may for example be a protein or peptide having at least a part of the amino acid sequence constituting the leucocidin M protein or a protein or peptide having at least a part of the amino acid sequence constituting the leucocidin F protein.

The protein or peptide having at least a part of the amino acid sequence refers to a protein or peptide having at least a part of the amino acid sequence represented by SEQ ID NO: 3 or SEQ ID NO: 4, and the lengths of the amino acid sequences of these proteins or peptides are not limited particularly as far as it is possible to impart a toxin-neutralizing activity to a ruminant animal as a subject animal.

In addition, the protein having at least a part of the amino acid sequence may have the amino acid sequence indicated by SEQ ID NO: 3 or SEQ ID NO: 4 having a variation introduced therein. In such a case, the degree of the variation in the protein having the variation introduced therein is not limited particularly as far as it is possible to impart a toxin-neutralizing activity to a ruminant animal as a subject animal, and the homology of the amino acid sequence of the protein having a variation introduced therein may for example be a homology of at least 70% or more, preferably 80% or more, more preferably 90% or more to the amino acid sequence of SEQ ID NO: 3 or SEQ ID NO: 4. The variation in the amino acid residues capable of being introduced in the amino acid sequence indicated by SEQ ID NO: 3 or SEQ ID NO: 4 may be a substitution, deletion, insertion, and/or addition of 1 to 2 amino acids. For example, the substituted amino acid is preferably an amino acid having a chemical property similar to that of the initial amino acid in order to keep the steric structure of the initial protein. Such a conservative substitution may typically include a mutual substitution between non-polar amino acids Ala, Val, Leu, Ile, Pro, Met, Phe, and Trp, a substitution between non-charged amino acids Gly, Ser, Thr, Cys, Tyr, Asn, and Gln, a substitution of an acidic amino acid Asp with Glu, and a mutual substitution by basic amino acids Lys, Arg, and His. The variation such as the deletion, insertion, and addition can be achieved also by using any known methods.

The protein employed in the present invention may not necessarily contain the entire amino acid sequence of a leucocidin M/F as far as it can impart a toxin-neutralizing activity equivalent to that of a naturally occurring leucocidin M/F, and the leucocidin M/F antigen is preferably be a protein or peptide having at least a part of the amino acid sequence constituting the leucocidin M protein and a protein or peptide having at least a part of the amino acid sequence constituting the leucocidin F protein.

The leucocidin M/F antigen can be prepared from a culture supernatant of the *Staphylococcus aureus*.

For example, the method described later in Examples is used to culture *Staphylococcus aureus* and a leucocidin M/F antigen can be obtained from the culture supernatant.

Alternatively, the leucocidin M/F antigen may be one obtained by a synthesis.

The synthesis can be conducted for example by a method employing a device such as an automated protein synthesizer or a full-automated peptide synthesizer.

The leucocidin M/F antigen which was prepared from a culture supernatant of *Staphylococcus aureus* or synthesized as described above may further be subjected to an enzymatic treatment for reducing the amino acid length or a modification of a certain amino acid as far as it can impart a toxin-neutralizing activity equivalent to that of a naturally occurring leucocidin M/F.

It is also possible that the leucocidin M/F antigen is one which has been subjected to an inactivation treatment.

For example, the leucocidin M/F antigen obtained from the culture supernatant can be imparted with a higher safety through an inactivation treatment since the leucocidin M/F antigen has a toxicity.

The method for inactivation treatment may be, but not limited to, a method for allowing the leucocidin M/F antigen to be in contact with formalin or phenol or to be subjected to warming or ultraviolet irradiation.

In addition, the immunogenic composition according to the present invention can prevent infection with cow mastitis more efficiently by containing a somatic antigen of *Staphylococcus aureus* in addition to the leucocidin M/F antigen.

The somatic antigen of *Staphylococcus aureus* may be an inactivated whole cell of *Staphylococcus aureus* or a part thereof.

The inactivation treatment of *Staphylococcus aureus* may be, but not limited to, a method for allowing the cells of *Staphylococcus aureus* to be in contact with formalin or phenol or to be subjected to warming or ultraviolet irradiation.

The part of the inactivated whole cells refers to one obtained by subjecting the inactivated whole cells to a treatment for degradation such as a physical treatment including an ultrasonic treatment or an enzymatic treatment using a hydrolase such as lysostaphin.

The *Staphylococcus aureus* may be any commercially available strains or strains archived to various research institutes. In case of a predetermined disease as a target of prevention or therapy, *Staphylococcus aureus* isolated from the site of the onset of the disease by a known method may also be used. In case for example of prevention of mastitis, *Staphylococcus aureus* separated from a milk of ruminant animal is preferred.

The immunogenic composition according to the present invention can appropriately be combined with pharmacologically acceptable vehicle or carrier, typically sterilized water, physiological saline, vegetable oils, emulsifiers, suspending agents, surfactants, stabilizers, and the like to form a formulation, thereby producing an antibody against a leucocidin M/F antigen or a somatic antigen of *Staphylococcus aureus* or enhancing the infection preventive effect. It is also possible to add various immunostimulator to the immunogenic composition according to the present invention.

The immunogenic composition can be produced by mixing the various components such as leucocidin M/F antigen, if necessary, a somatic antigen of *Staphylococcus aureus*.

The immunogenic composition according to the present invention can preferably be employed as a vaccine for a ruminant animal which is affected adversely if infected with *Staphylococcus aureus*.

The adjuvant to be incorporated when using an immunogenic composition according to the present invention as a vaccine may for example be an inorganic substance such as aluminum gel adjuvant, a microorganism or a microorganism-derived substance (BCG, muramyl dipeptide, *Bordetella pertussis*, pertussis toxin, cholera toxin, and the like), a surface active substance (saponin, deoxycholic acid, and the like), an emulsion of an oily substance (mineral oil, vegetable oil, animal oil), which may be used independently or in a combination of two or more. As an adjuvant to be incorporated into the immunogenic composition according to the present invention, an oil adjuvant is preferred. More preferably, an oil adjuvant whose main component is squalane is employed, typically anhydrous mannitol oleate-supplemented squalane liquid which is preferable also from the safety point of view. The effect of this adjuvant is remarkable unexpectedly, and incorporation of this adjuvant enables achievement of an excellent preventive effect against *Staphylococcus aureus* and a high safety.

The anhydrous mannitol oleate-supplemented squalane liquid refers to a solution consisting of anhydrous mannitol oleate and squalane.

Furthermore, the immunogenic composition according to the present invention can be used also for preparing a formulation for treatment or prevention of diseases related to *Staphylococcus aureus* in ruminant animals.

The diseases related to *Staphylococcus aureus* are not limited particularly and may for example be mastitis, purulent diseases, arthritis, conjunctivitis, dermatitis, and the like.

As used herein, the treatment refers to that, in a ruminant animal which has already exhibited the onset of the disease as a result of infection with *Staphylococcus aureus*, a cure or a remission of the relevant symptoms is achieved.

The prevention refers to that, in a ruminant animal which has already been infected with *Staphylococcus aureus* but is still in a condition before the onset of the disease, the onset is prevented by a preventive administration to the ruminant animal.

It is also possible to induce an immune response to *Staphylococcus aureus* by administering an immunologically effective amount of the immunogenic composition to a ruminant animal as a subject animal.

An "immunologically effective amount" refers to an amount of an antigen or an immunogenic composition sufficient for inducing a cell-mediated immune response (T cell) or a humoral immune response (B cell or antibody) or the both immune responses as measured by a standard assay known to those skilled in the art.

The administration of the immunogenic composition according to the present invention to an animal can be conducted for example via intraarterial injection, intravenous injection, subcutaneous injection, or intranasally, intratracheally, intramuscularly, or orally by any methods known to those skilled in the art. While the dose may vary depending on the body weight or age of the ruminant animal and administration method, purpose of use, and the like, those skilled in the art can select a suitable dose appropriately.

EXAMPLES

[Test Strain Selection]

Upon selection of test strain for *Staphylococcus aureus*, those satisfying the following conditions are employed.

1. Strains isolated from the milk of a cow developing mastitis possibly caused outdoor by *Staphylococcus aureus*. The method for identifying *Staphylococcus aureus* is in accordance with a general identification method. Inoculation of about 200 CFU to a breast of a cow causes the onset of acute mastitis.

2. Strains identified as having CP5 type·MLST typing-based-CC97 type based on gene profile and also having a leucocidin M/F. Otherwise, possession of genes of known pathogenic factors such as fibronectin-binding protein, clumping factor gene, and the like is also included.

3. Strains whose culture supernatants exhibit potent cytotoxic activities to bovine neutrophils when compared with that of a strain having no leucocidin M/F.

[Preparation Method for Immunogen]

1. Preparation of Whole Somatic Antigen and Leucocidin M/F Antigen

The culture of *Staphylococcus aureus* can be obtained by inoculating the inoculant to a liquid medium such as Brain Heart Infusion broth (BHI medium) followed by incubation with shaking at 37° C. for 18 to 24 hours. This is not limitative and any known culture method can be utilized as far as the cell count reaches $10^9$ CFU/mL or higher or the expression of a CP antigen or leucocidin is observed.

2. Preparation Method for Whole Somatic Antigen

The whole somatic antigen, after being collected by centrifugation of the bacterial culture fluid, is inactivated by adding formalin (formaldehyde) to effect sensitization at 37° C. for 24 hours. The concentration of formalin may be within the range allowing the inactivation to be achieved without damaging the antigenicity.

3. Preparation Method for Leucocidin M/F Antigen

From the bacterial culture fluid, the supernatant is collected by cooling centrifugation and the sediment is recovered by ammonium sulfate method and dissolved in PBS and then dialyzed. The concentration of ammonium sulfate may be within the range enabling the sedimentation of leucocidin M/F fractions. It is also possible to use other method such as a polyethylene glycol method. To the resultant concentrated leucocidin M/F, formalin (formaldehyde) is added to effect sensitization at 37° C. for 24 hours, thereby achieving inactivation.

4. Preparation of Antigen

For the amount of the antigen, $4 \times 10^{10}$ CFU/dose of inactivated cells as cells before inactivation is used per injection. In addition to this, the inactivated concentrated supernatant is added as a leucocidin toxin activity before inactivation so that the amount of the antigen is 5120 U/dose.

The leucocidin toxin activity was measured according to the following procedure.

1) Polymorphonuclear (PMN) Leukocyte and Leucocidin

PMN leukocytes were prepared from bovine peripheral blood by centrifugation using Ficoll (Pharmacia). For a positive control, the supernatant of the bacterial fluid obtained by culturing BM1006 strain isolated from a bovine milk in a BHI medium at 37° C. for 20 hours (leucocidin toxin activity: x 320 equivalent) was used as a leucocidin reference solution.

2) Measurement of Leucocidin Toxin Activity (PMN Assay)

According to the aforementioned 1), PMN leukocytes were prepared from bovine peripheral blood and mixed with respective analytes which had been subjected to the serial dilution in a flat bottom 96-well plate. Based on the maximum dilution magnitude exhibiting 50% or more of cytotoxicity per well, the leucocidin toxin activities of the analytes were determined.

3) Measurement of Leucocidin Neutralizing Antibody

The analyte which had been subjected to a 2-fold dilution with RPMI-GH (RPMI1640+0.1% gelatin+20 mM HEPES) as a diluent in the flat bottom 96-well plate was combined with an equal amount of the leucocidin reference solution which had been subjected to 50-fold dilution with RPMI-GH, thereby effecting sensitization at 37° C. for 60 minutes. After adding 80 µL of the neutralizing sensitization solution to a gelatin-coated flat bottom 96-well plate, 20 µL of the PMN leukocyte-containing solution adjusted at $4 \times 10^6$ cell/mL was added and stirred using a plate mixer and then sensitized at 37° C. When 50% or more of cytotoxicity per well was observed, the result was judged as leucocidin toxin activity positive, and based on the maximum dilution magnitude which inhibit the leucocidin toxin activity, the leucocidin antibody titer of the analyte was determined. In the present invention, the test sample which gave, when administering the test sample to a cow, a significant elevation by 4-times or more of the leucocidin antibody titer in the analyte when compared with a control cow to which no test sample was administered is judged to "be able to impart the leucocidin toxin-neutralizing activity."

5. Use of Adjuvant

When using a vaccine, an adjuvant for imparting an immune against the active component to a milk is added. While a mineral oil- or vegetable oil-based oily adjuvant is employed primarily, it may be combined with an aluminum gel adjuvant and the like.

(Example 1) Strain Selection

1. MLST Analysis and Leucocidin Gene Analysis

From *Staphylococcus aureus* which had been isolated from the bovine milk and then identified, a DNA was extracted by a general method such as phenol-chloroform extraction/ethanol precipitation method, boiling method, or a method using a commercially available kit, and then subjected to a MLST typing method. MLST typing method is a molecular epidemiological analysis procedure based on the base sequence which enables determination and analysis of subspecies of bacteria isolates or other microorganisms, and was conducted and analyzed in accordance with MLST typing method (http://www.mlst.net/). Leucocidin gene possession surveillance was conducted in accordance with the method described in Hata et al., J Clin Microbiol. 2010.482130-2139 2003; 10(2):272-277.

2. Evaluation of Neutrophil Cytotoxic Activity of Culture Supernatant

A candidate strain was inoculated to a cell proliferation medium (Brain Heart Infusion Porcine broth) and cultured at 37° C. for 24 hours with shaking to obtain a supernatant, which was subjected to a serial dilution with a commercially available EAGLE minimum essential medium (Eg-MEM) and then combined with an equal amount of the granulocyte cells which was collected from bovine peripheral blood and then purified, thereby effecting sensitization at 37° C. for 2 hours. Using the maximum dilution magnitude exhibiting a granulocyte degenerative effect as a leucocidin toxin activity, the toxin activity of the candidate strain supernatant was evaluated.

Leucocidin E-leucocidin D complex (LukE-LukD), hemolysin (hlg), leucocidin M and/or leucocidin F (LukM (/F)) were analyzed for their presence or absence in the supernatant based on a known procedure, and indicated with "+" in the table if detected.

The results are shown in Table 1.

Based on the results shown in Table 1, the *S. aureus* HK-3 strain which was typed as CC97 type in MLST typing and possessed the leucocidin M/F gene and whose toxin activity was excellent was selected and subjected to the following tests.

TABLE 1

Test strain selection

| Strain | Origin | Supernatant LukE-LukD | hlg | LukM (/F) | Toxin activity 2) | MLST type |
|---|---|---|---|---|---|---|
| S. aureus No. 1 | Bovine milk of Kyoto | + | + | | <40 | CC97 |
| S. aureus No. 2 | 1) | + | + | | <40 | CC97 |
| S. aureus No. 4 | 1) | + | + | | <40 | CC126 |
| HK-1 | Bovine milk of Oita | + | + | | 40 | CC15 like |
| HK-3 | 1) | + | + | + | 5120 | CC97 |
| HK-4 | 1) | + | + | + | 2560 | CC97 |
| HK-5 | 1) | + | + | + | 2560 | CC97 |
| HK-6 | 1) | + | + | + | 2560 | CC97 |
| HK-7 | 1) | + | + | | <40 | CC97 |
| HK-8 | 1) | + | + | | <40 | CC15 |
| HK-9 | 1) | + | + | + | 640 | CC97 |
| HK-10 | 1) | + | + | | <40 | CC15 |
| BM1001 | National Institute of Animal Health 3) | + | + | + | 320 | CC705 |
| BM1006 | Bovine milk | + | + | + | 640 | CC97 |

1) Strain isolated by Institute of Microbial Chemistry
2) Unit: U/mL
3) National Institute of Animal Health, National Agriculture and Food Research organization (Example 2) Preparation Method for Typical Immunogen 1. Preparation of Inactivated Whole Somatic Antigen
Cell Culture:
S. aureus HK-3 strain obtained in Example 1 was inoculated in an agar medium for production (Brain Heart Infusion Porcine+Bacto Agar), and cultured statically at 37° C. for 24 hours. The grown colonies were picked up and transferred to a liquid medium for production (Brain Heart Infusion Porcine) and cultured with shaking at 37° C. for 18 to 24 hours, and then used as main bacterial culture fluids if their cell counts reached $2 \times 10^9$ CFU/mL or more.
Preparation of Inactivated Whole Somatic Antigen Solution:
To the main bacterial culture fluid, formalin (formaldehyde) was added at 0.4% by volume and sensitization was conducted at 37° C. for 24 hours. After sensitization, the cell count was adjusted at 1 to $3 \times 10^{11}$ CFU/mL appropriately using PBS, and the fluid was subjected to Example 3, Example 5-1, and Example 5-2 described below.
2. Preparation of Leucocidin M/F Concentrated Inactivated Antigen
From the main bacterial culture fluid, the supernatant was collected by cooling centrifugation and the sediment was recovered by ammonium sulfate method, dissolved in PBS and dialyzed to obtain a leucocidin M/F antigen. The resultant leucocidin M/F antigen was validated to contain the leucocidin M protein represented by SEQ ID NO: 3 and the leucocidin F protein represented by SEQ ID NO: 4 by conducting a western blotting using antisera prepared based on the respective recombinant proteins prepared based on SEQ ID NO: 3 and SEQ ID NO: 4. After adjusting the leucocidin toxin activity as 25,600 U/mL or more, formalin (formaldehyde) was added at 0.2% by volume and sensitized at 37° C. for 24 hours, and then subjected to Example 4, Example 5-1, and Example 5-2 described below.
The inactivated state of the antigen after formalin sensitization was validated by observing the loss of the toxin activity by measuring the leucocidin toxin activity.

(Example 3) Onset Prevention Test Using HK-3 Strain Inactivated Somatic Antigen

Among the immunogens prepared in Example 2, the inactivated whole cells were used to prepare a vaccine, which was injected to a milking cow (Holstein, 5-year old), and thereafter the preventive effect on the intramammary infection was compared with that in a control cow (non-vaccinated cow).
As an inactivated whole cell vaccine, an inactivated bacteria-containing fluid adjusted at $4 \times 10^{10}$ CFU as a cell count before inactivation in a volume of 2 mL per injection was added, and the same supplemented with the adjuvant was injected intramuscularly twice at an interval of 4 weeks. As a viable cell challenge test, an intramammary inoculation of 500 CFU of S. aureus HK-3 strain was made 2 weeks after immunizing twice. After viable cell inoculation, time-course evaluation was made for the milk somatic cell count as a mastitis symptom index and the milk-excreted cell count as an infection index. The results are shown in FIG. 1.
Based on the results shown in the upper and lower figures in FIG. 1, the test cow's breasts 1 and 2 which were treated by HK-3 strain inactivated somatic antigen vaccine, exhibited, when compared with breasts 1 and 2 of the control cows, an earlier recovery from somatic cell count increase and a milk-excreted cell count reducing effect in an earlier stage of the infection, whose degrees were however only limited. Therefore, it was decided that inactivated somatic antigen vaccine itself was not sufficient for achieving a prevention effect for suppressing the onset of the disease caused by Staphylococcus aureus in bovine breasts.

Figure 2:
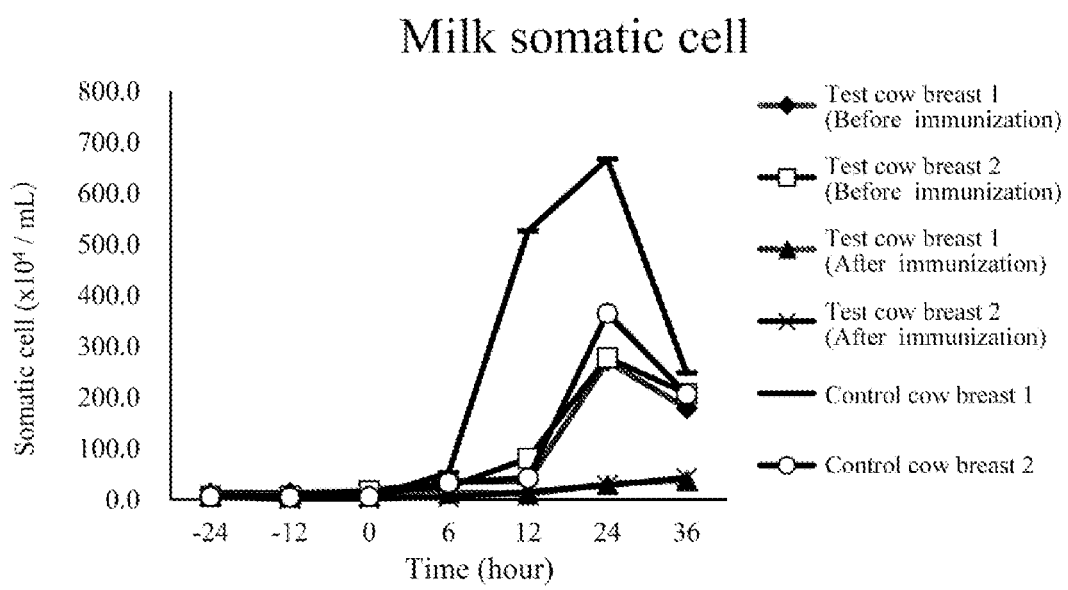
FIG. 2 is a graph showing the results of the inflammatory effect reduction test conducted in Example 4 on the supernatant components using concentrated inactivated antigen of the leucocidin M/F. In the upper figure, the ordinate indicates somatic cell count per mL of the milk and the abscissa indicates the time (h). In the lower figure, the ordinate indicates bacterial cell count per mL of the milk and the abscissa indicates the time (h) (the same applies to the upper and lower figures in FIG. 4).
Figure 2:
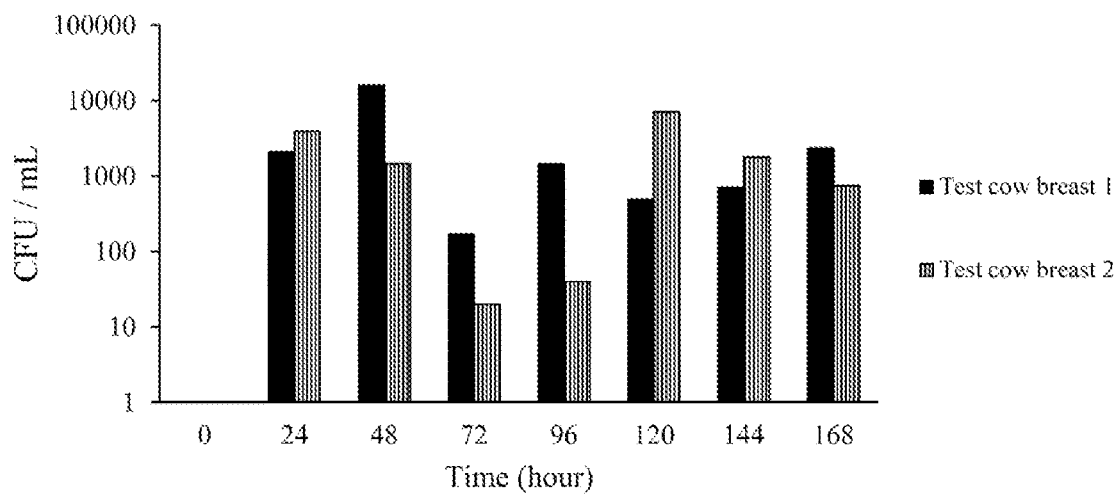

(Example 4) Inflammatory Effect Reduction Test for Supernatant Component Using Leucocidin M/F Concentrated Inactivated Antigen Among the immunogens prepared in Example 2, the leucocidin M/F concentrated inactivated antigen was used to prepare a vaccine, and the vaccine was injected in a milking cow (Holstein, 3-year old). Before and after the injection, an intramammary inoculation of the supernatant components containing the leucocidin M/F was conducted for comparing the inflammation reducing effect. As a leucocidin M/F concentrated inactivated antigen vaccine, 5120 U of leucocidin M/F concentrated inactivated antigen as leucocidin toxin activity before inactivation in a volume of 2 mL per injection was used, and the same supplemented with the adjuvant was injected intramuscularly twice at an interval of 4 weeks. As a supernatant inoculation test, an intramammary inoculation of 1280 CFU of a concentrated supernatant of S. aureus HK-3 strain was made before immunization and 2 weeks after immunizing twice. After the concentrated supernatant inoculation, the milk somatic cell count was evaluated as a mastitis symptom index. The results are shown in FIG. 2.
Based on the results shown in the upper and lower figures in FIG. 2, the concentrated supernatant inoculation triggered a severe inflammation reflected by a somatic cell count (SCC, number of cells in milk mainly consisting of leukocyte and epithelial cells) exceeding 5,000,000/mL in breasts 1 and 2 of a test cow before vaccine injection (before immunization) and a control cow (non-vaccinated cow). On the other hand, the somatic cell count was reduced substantially after injection of leucocidin M/F concentrated inactivated antigen vaccine prepared from HK-3 strain, indicating a significantly reduced breast inflammation.
Subsequently, this test cow received an intramammary inoculation of S. aureus HK-3 strain by a method similar to that described in Example 3. As a result, the breasts 1 and 2 of the cow receiving the injection of the M/F concentrated inactivated antigen vaccine exhibited no milk-excreted cell count reducing effect.
Based on these results, the leucocidin M/F concentrated inactivated antigen exhibited an inhibitory effect on the inflammation triggering by S. aureus HK-3 strain, which means it was successful in imparting a toxin-neutralizing activity to the test cow. However, the Staphylococcus aureus excretion level was not reduced significantly, showing no infection preventive effect. Accordingly, it was proven that the leucocidin M/F concentrated inactivated antigen has an ability of reducing the severity of a disease caused by Staphylococcus aureus.

(Example 5-1) Infection Prevention Test Using Leucocidin M/F Concentrated Inactivated Antigen Together with Inactivated Whole Somatic Antigen Among the immunogens prepared in Example 2, the inactivated whole cells and the leucocidin M/F concentrated inactivated antigen were used to prepare a vaccine, which was injected to a milking cow (Holstein, 4-year old), and thereafter the preventive effect on the intramammary infection was compared with that in a control cow (non-vaccinated cow).

As an inactivated whole cell vaccine, an inactivated bacteria-containing fluid adjusted at $4\times10^{10}$ CFU as a cell count before inactivation in a volume of 2 mL per injection was added together with a 5120 U of leucocidin M/F concentrated inactivated antigen as a leucocidin toxin activity before inactivation, and the same supplemented with the adjuvant was injected intramuscularly twice at an interval of 4 weeks. The levels of the ELISA antibody against the whole cell and the neutralizing antibody against the leucocidin in the milk after 2 injections in the test cow after the vaccine injection indicated that significantly high antibodies were imparted against both of the whole cell and the leucocidin when compared with the test cow before vaccine injection and the non-vaccinated control cow.

These results are shown in Table 2.

The antibody titer of the bovine serum to the cells was measured here by an indirect ELISA method using 1 to $3\times10^7$ CFU of the inactivated whole somatic antigen prepared by a method similar to that in Example 2 as an antigen.

As a viable cell challenge test, an intramammary inoculation of 500 CFU of *S. aureus* HK-3 strain was made to a control cow and a test cow 2 weeks after immunizing twice. After viable cell inoculation, time-course evaluation was made for the milk somatic cell count as a mastitis symptom index and the milk-excreted cell count as an infection index. The results are shown in FIG. 3.

Figure 3:
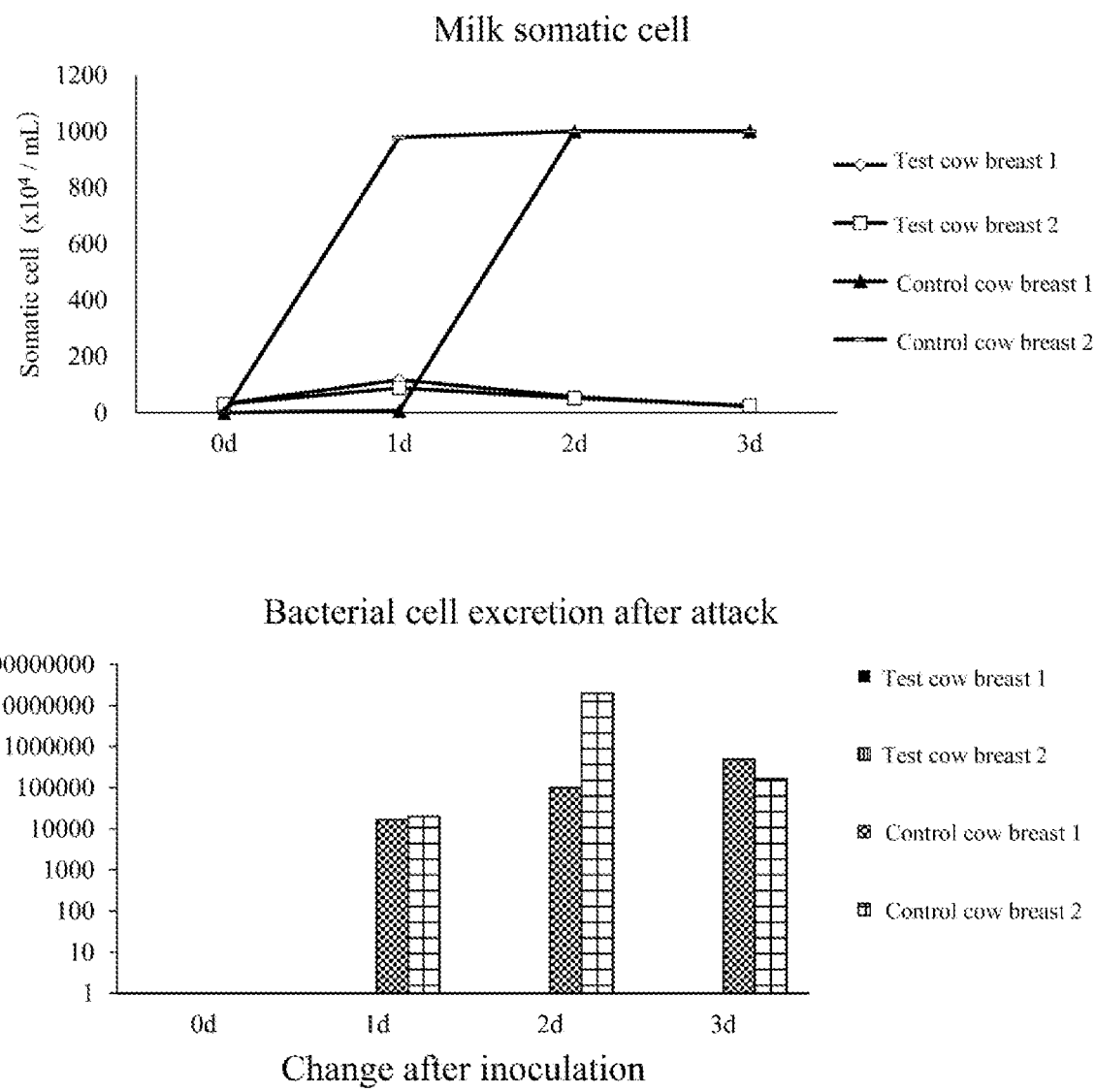
FIG. 3 is a graph showing the results of the infection prevention test conducted in Example 5-1 using the concentrated inactivated antigen of the leucocidin M/F and the inactivated whole somatic antigen.

Based on the results shown in the upper and lower figures in FIG. 3, leucocidin M/F concentrated inactivated antigen- and inactivated whole somatic antigen-treated test cow's breasts 1 and 2 exhibited, when compared with breasts 1 and 2 of the control cows, a significant reduction in the somatic cell count at an early stage of the infection, while no milk-excreted cell count was observed.

Based on these results, combination of the leucocidin M/F concentrated inactivated antigen and the HK-3 strain inactivated somatic antigen exerts the effect to further reduce the severity of a disease caused by *Staphylococcus aureus* together with an infection preventive effect when compared with the leucocidin M/F concentrated inactivated antigen when used alone.

TABLE 2

Antibody titer after 2 vaccine injections

| | ELISA antibody titer to bacterial cells | | | Leucocidin antibody titer |
|---|---|---|---|---|
| | Total IgG | IgG2 | IgM | |
| Test cow (before vaccine injection) | 35.7 | 67.6 | 639 | 7.1 |
| Test cow (after 2 vaccine injections) | 538 | 257 | 1145 | 40 |
| Control cow (non-vaccinated cow) | 30.9 | 50.0 | 294 | 7.1 |

(Example 5-2) Infection Prevention Test Using Leucocidin M/F Concentrated Inactivated Antigen Together with Inactivated Whole Somatic Antigen To a test cow 2 weeks after immunizing twice by a method similar to that in Example 5-1 and also to a control cow, an intramammary inoculation of 100 CFU of *S. aureus* HK-3 strain was made as a viable cell challenge test. After the viable cell inoculation, time-course evaluation was made for the milk somatic cell count as a mastitis symptom index and the milk-excreted cell count as an infection index. The results are shown in FIG. 4.

Figure 4:
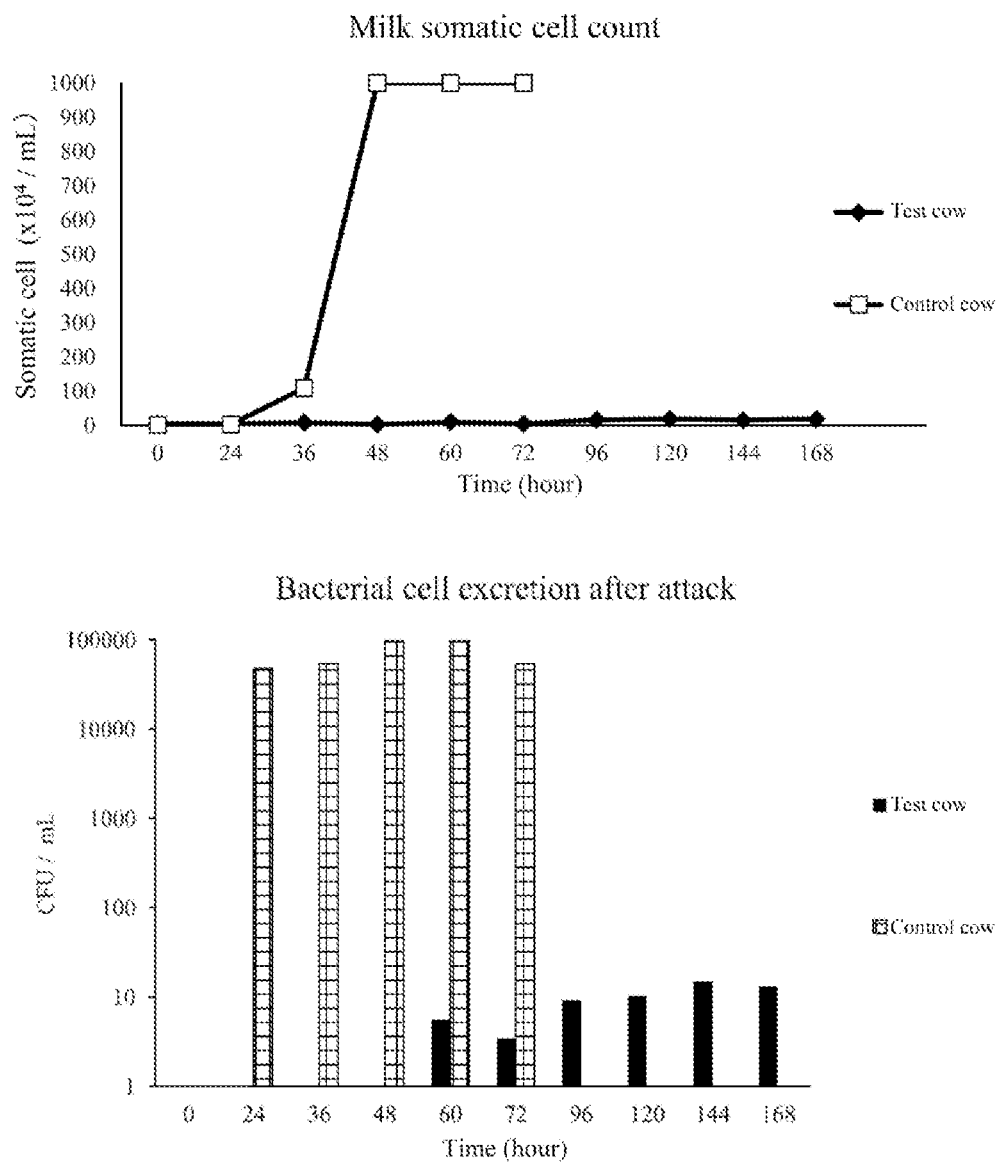
FIG. 4 is a graph showing the results of the infection prevention test conducted in Example 5-2 using the concentrated inactivated antigen of the leucocidin M/F and the inactivated whole somatic antigen.

Based on the results shown in the upper and lower figures in FIG. 4, the breasts of the test cow receiving the leucocidin M/F concentrated inactivated antigen and the inactivated whole somatic antigen exhibited a significant reduction in both of the somatic cell count and the milk-excreted cell count when compared with the breasts of the control cow.

Based on these results, combination of the leucocidin M/F concentrated inactivated antigen and the HK-3 strain inactivated somatic antigen exerts the effect to further reduce the severity of a disease caused by *Staphylococcus aureus* together with an infection preventive effect when compared with the leucocidin M/F concentrated inactivated antigen when used alone.

The invention claimed is:

1. An immunogenic composition comprising inactivated whole cell *Staphylococcus aureus* and concentrated inactivated leucocidin M/F antigen capable of imparting a toxin-neutralizing activity to a ruminant animal as a subject animal, the inactivated leucocidin M/F antigen including a leucocidin M protein comprising an amino acid sequence represented by SEQ ID NO: 3, in which one or two amino acids may be substituted, deleted, inserted, and/or added, and a leucocidin F protein of SEQ ID NO: 4, in which one or two amino acids may be substituted, deleted, inserted, and/or added.

2. The immunogenic composition according to claim 1, wherein the leucocidin M/F antigen is obtained from a culture supernatant of *Staphylococcus aureus*.

3. The immunogenic composition according to claim 1, wherein the leucocidin M/F antigen is synthesized.

4. The immunogenic composition according to claim 1, wherein the *Staphylococcus aureus* is a *Staphylococcus aureus* separated from a milk of the ruminant animal.

5. The immunogenic composition according claim 1, wherein the ruminant animal is a cow, a goat, a sheep, or a deer.

6. The immunogenic composition according to claim 1 for use as a vaccine.

7. The immunogenic composition according to claim 1 for use in preparing a formulation for treatment or prevention of diseases related to *Staphylococcus aureus* in the ruminant animal.

8. A method for inducing an immune response to *Staphylococcus aureus*, the method comprising administrating the immunogenic composition according to claim 1 in an immunologically effective amount to a ruminant animal as a subject animal.

9. The method according to claim 8, wherein the immune response prevents or reduces a disease or a symptom relating to the *Staphylococcus aureus* in the ruminant animal.

\* \* \* \* \*